US011401184B1

(12) United States Patent
Guy et al.

(10) Patent No.: US 11,401,184 B1
(45) Date of Patent: *Aug. 2, 2022

(54) COMPARATIVE METHOD OF MAINTAINING A SAFE LEVEL OF CHLORINE IN A BODY OF WATER

(71) Applicant: King Technology Inc., Hopkins, MN (US)

(72) Inventors: David Guy, Maple Grove, MN (US); Jeffrey D Johnson, Edina, MN (US); Joseph King, Wayzata, MN (US)

(73) Assignee: KING TECHNOLOGY INC.

( * ) Notice: Subject to any disclaimer, the term of this patent is extended or adjusted under 35 U.S.C. 154(b) by 137 days.

This patent is subject to a terminal disclaimer.

(21) Appl. No.: 16/974,052

(22) Filed: Sep. 18, 2020

Related U.S. Application Data

(60) Provisional application No. 62/908,611, filed on Oct. 1, 2019.

(51) Int. Cl.
*C02F 1/76* (2006.01)
*G01N 33/18* (2006.01)
*C02F 103/42* (2006.01)

(52) U.S. Cl.
CPC ............... *C02F 1/76* (2013.01); *G01N 33/18* (2013.01); *C02F 2103/42* (2013.01); *C02F 2209/29* (2013.01); *C02F 2303/04* (2013.01)

(58) Field of Classification Search
CPC ..... C02F 1/76; C02F 2103/42; C02F 2209/29; C02F 2303/04; G01N 33/18
USPC ............ 210/167.11, 739, 753, 754, 755, 756
See application file for complete search history.

(56) References Cited

U.S. PATENT DOCUMENTS

| | | | | |
|---|---|---|---|---|
| 3,170,883 | A * | 2/1965 | Owen | C02F 1/76 424/661 |
| 4,614,595 | A * | 9/1986 | Azzarella | C02F 5/08 210/765 |
| 11,203,539 | B1 * | 12/2021 | Guy | C02F 1/76 |
| 2004/0082633 | A1 * | 4/2004 | Howarth | C02F 1/50 514/389 |
| 2007/0272622 | A1 * | 11/2007 | Mercer | C02F 1/76 210/754 |
| 2009/0200246 | A1 * | 8/2009 | King | A01N 59/16 422/255 |
| 2019/0375658 | A1 * | 12/2019 | Ness | B01F 25/4315 |

* cited by examiner

*Primary Examiner* — Fred Prince
(74) *Attorney, Agent, or Firm* — Johnson & Phung LLC

(57) ABSTRACT

A method of maintaining a body of water in a usable condition through a comparative measurements of total chlorine and free chlorine in the body of water to determine if a synergistic chemical combination exists within the body of water that can effect the amount of chlorine to add to the body of water.

11 Claims, 1 Drawing Sheet

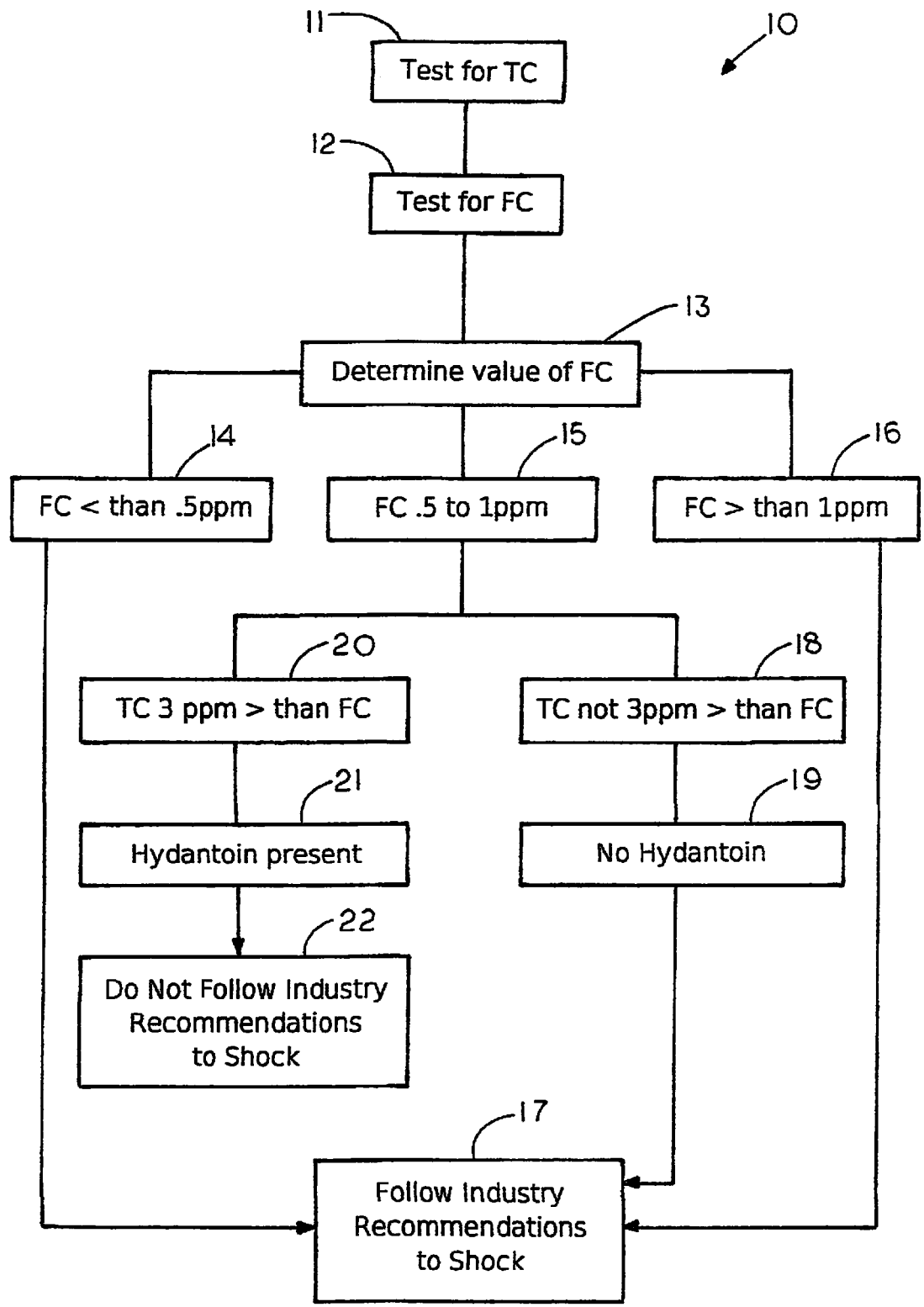

COMPARATIVE METHOD OF MAINTAINING A SAFE LEVEL OF CHLORINE IN A BODY OF WATER

CROSS REFERENCE TO RELATED APPLICATIONS

This application claims priority from U.S. Provisional application 62/908,611 filed Oct. 1, 2019.

STATEMENT REGARDING FEDERALLY SPONSORED RESEARCH OR DEVELOPMENT

None

REFERENCE TO A MICROFICHE APPENDIX

None

FIELD OF THE INVENTION

This invention is a comparative method on how to maintain a body of recreational water if it is unknown if the body of water contains a synergist chemical combination where the difference between the free chorine and the total chlorine in the body of water may inaccurately reflect when to shock the body of water or add chlorine to the body of water.

BACKGROUND OF THE INVENTION

Chlorine is a well-known sanitizer that is added to water in swimming pools or hot tubs to rid the water of harmful organisms and containments. One of the byproducts of adding chlorine is the formation of chloramines in the water as a result of the chlorine reacting with containments in the water. Part of the ongoing process of maintaining the water in pools or hot tubs in a safe state includes periodically riding the water of the chloramines through a process known as "shock" or "super chlorination" of the water. A typically industry recommendation on the amount of chlorine to shock the water, which is sometimes referred to as super chlorinating, is to add a dose of chlorine to water that is about ten times the measured amount of chloramines in the water. A number of industry publication provide guidance on when a person should shock the water to rid the water of chloramines based on various factors such as pool use or the level of chlorines in the body of water.

Typically, those who maintain the pools or hot tubs often lack the necessary chemical background to fully understand why and when to shock the water to keep the water in a safe usable condition. As a result those who maintain pools or hot tubs typically rely on industry organizations to provide guidelines on when to add chlorine as well as how and when to "shock" the water to make the water safe for use.

One such group that provides guidelines is the American Chemistry Council, which advises owners that in a system using chlorine as a sanitizer the "free available chlorine [FAC] in the system should be in the range of 2-4 ppm, but never fall below 1.0 ppm" and that the system should be shocked when the combined chlorine (CC) is greater than 0.2 ppm.

Other companies such as Taylor Technologies, Inc. of Sparks, Md. 21152 sell test kits that includes a guide that contains recommendations on an acceptable level of 14 different water parameters, which are based on recommendations by the American Swimming Coaches Association. The Taylor Technologies guide references the National swimming Foundation CPO handbook as it recommends that when chlorine is uses as the sanitizer in a residential hot tub, the level of free chlorine should be between 2 ppm and 10 ppm with the ideal range of free chlorine between 3 ppm and 5 ppm. The guide recommends shocking the pool when the difference between the TAC and the FAC (i.e. CC) is greater that 0.3-ppm.

Other recommendations found in the literature, which are based on measured levels chlorine, include the Washington County MN fact sheet on "Proper Super chlorination of pools" that states the pool water should be shocked if the combined chlorine exceeds 1 ppm and the Swim University publication that recommends one to keep the combined chloramines less than 0.2 ppm.

Other recommendations on how to maintain and when to shock the water in a pool or hot tub are based on use rather than a determination of the amount of chloramines in the body of water. For example, Bioguard, which sells a shock product, recommends that "to prevent pool problems, shock at least once per week during periods of heavy use or when water temperatures are above 80° Fahrenheit and once every two weeks in resident pools receiving normal use".

The above consist of a group of typical well known "industry recommendations on when to shock". Unfortunately, the "industry recommendations on when to shock, which are available to the public from various organizations as well as the Internet, is often based on "a one size fits all" that ignores the effect that synergist chemical combinations may exist in the water that affect the "industry recommendations on when to shock".

Consequently, such "industry recommendations on when to shock" which are based on "one size fits all" instructions can in certain circumstances lead to improper shocking as well as causing an unnecessarily high level of free chlorine in the body of water, which is an undesirable effect in pools and particularly in hot tubs since high water temperature in hot tubs or spas opens skin pores, which may increase the chances of adverse chlorine effects such as nausea, itchy eyes, skin redness as well as other effects.

Typically, "industry recommendations on when to shock" rely on the difference between the total chlorine and the free chlorine. The "industry recommendations on when to shock" as described above measure a parameter or parameters associated with a body of water such as a hot tub or pool but fail to consider that the body of water may contain a hydantoin, which can lead to an incorrect recommendation on maintaining the body of water in a hot tub or pool in a safe user friendly condition. That is, a hydantoin within the body of water that can have an adverse effect on the industry recommendations, which are based solely on differences between the total chlorine and the free chlorine in the body of water.

In contrast to the industry recommendations on when to add chlorine, which are based on the measured differences between total chlorine and free chlorine in the body of water, the "comparative method" described herein is based on comparative values of total chlorine and the free chlorine in the body of water to determine when to add chlorine to the body of water.

BRIEF DESCRIPTION OF THE DRAWINGS

FIG. 1 shows a flow chart of the "comparative method" for maintaining a body of water for human immersion through addition of chlorine, where a sanitizing content of the body of water other than a presence of chlorine in the body of water is unknown.

DESCRIPTION OF THE PREFERRED EMBODIMENT

The invention described herein is a method for pool or hot tub maintenance that determines when to shock or add chlorine to a body of water, such as a pool or hot tub, when it is not known if the body of water contains a hydantoin. The method described herein is not based on the prior art method of obtaining a "measured difference" between the total chlorine and the free chorine (i.e. combined chlorine) in a body of water or the use of the body of water. In contrast to the prior art method of "a measured difference" between total chlorine and free chlorine the "comparative method" described herein is based on comparative values of total chlorine and free chlorine in the body of water.

The prior art i.e. "industry recommendations" on adding chlorine to a body of water fail to take into consideration that a hydantoin may be present in the body of water while the "comparative method" described herein takes into consideration that there may be a hydantoin in the body of water. The "comparative method" method described herein uses the unique relationship between the measured value of the total chlorine in a body of water and the measured value of free chlorine in the body of water when there is a hydantoin in the body of water to determine if chlorine should be added to the body of water in accordance with either "industry recommendations" or if chlorine should be added to the body of water in accordance with a body of water that contains a hydantoin. The "industry recommendations" as described herein do not take into consideration that a hydantoin in the body of water can create a synergistic chemical combination in a body of water that has an adverse effect on when to shock or add chlorine since the industry recommendations are based on differences between a measured value of the total chlorine and a measured value of the free chlorine in the body of water (i.e. combined chlorine) that do not take into consideration the effect of a hydantoin in the body of water.

The "comparative method" described herein recognizes that the existing industry recommendations on the method of maintaining the water in a body of water such as hot tub or a swimming pool in a safe condition, which relies on "measured differences" between total chlorine and free chlorine in the body of water, is not always correct since the existing industry method ignores the effect of a hydantoin in the body of water. In contrast, the "comparative method" described herein does not rely on a measured difference between the total chlorine and the free chlorine in the body of water to determine when to shock the body of water or add chlorine to the body of water. The "comparative method" enables one to determine when the industry recommendations on shocking or adding chlorine should be followed or when the industry recommendations on shocking or adding chlorine should not be followed.

In the first step in the "comparative method" one determines if the measured level of free chlorine in a body of water falls within any of three select ranges.

In the second step in the "comparative method" one compares the differences in the level of total chlorine in the body of water to the level of free chlorine in the body of water in order to determine if "industry recommendations" should or should not be followed.

FIG. 1 shows a flow chart 10 that illustrates the steps in the "comparative method" that enables one to determine when to add chlorine to shock the water in a pool or hot tub based on whether there is or is not a hydantoin in the body of water. The "comparative method" recognizes that if there is a hydantoin within the body of water, which can produce a synergistic chemical combination, one can determine the presence of a hydantoin in the body of water without an actual measurement of the hydantoin within the body of water. That is, if the body of water contains a hydantoin it has been found that the hydantoin can produce a synergistic combination that has an effect on the minimum level of free chlorine one needs to maintain the body of water in a safe condition for human immersion. The synergistic condition of a hydantoin in the body of water has a beneficial effect of allowing one to maintain the body of water where a measured level of free chlorine in the body of water can be maintained at least 50% less than conventional industry recommendations. Consequently, the difference between the total chlorine and the free chlorine in the body of water may provide incorrect recommendations on when to shock or add chlorine to the body of water.

Industry recommendations on methods of adding chlorine or determining when to shock the body of water are based on measured or assumed differences between the total chlorine level in the body of water and the level of free chlorine in the body water (i.e. combined chlorine) and do not take into account that there may be a hydantoin in the body of water. Consequently, industry recommendations are a "one size fits all" recommendation that may cause over chlorination, which may lead to adverse health effects. That is, when a person is immersed in a body of water such as a hot tub or spa the hot water opens skin pores that may increase the chances of adverse health effect such as nausea, itchy eyes, skin redness as well as other effects from high levels of chlorine.

In the "comparative method" described herein, which is illustrated in FIG. 1, one determines when to add chorine or when to shock the body of water when it is unknown if the body of water contains a hydantoin.

In the first step in the comparative method described herein one measures the level of total chlorine (TC) 11 and also measures the level of free chlorine (FC) 12 in the body of water using commercially available test kits that are commonly used in pool and hot tub industry to measure the level of total chlorine (TC) and the level of free chlorine (FC) in the body of water. However, in prior art industry methods to determine when to shock or add chlorine one subtracts the free chlorine (FC) in the body of water from the total chlorine (TC) in the body of water to determine the chloramines in the body of water.

The difference, which are considered chloramines, is used to determine when to shock as well as when to add chlorine to the body of water. These industry recommendations are referred herein as "one size fits all" industry recommendations. Unfortunately, if the body of water contains a hydantoin the determination of the difference between the level of total chlorine and the level of free chlorine (i.e. Tc-Fc), which is assumed to be the amount of chloramines in the body of water, may lead to over chlorination since the differences between the total chlorine and the free chlorine do not take into consideration that the presence of a hydantoin within the body of water that can produce a synergistic combination within the body of water that has an effect on the level of free chlorine to maintain in the body of water.

In the first step of the comparative method described herein one measures the value of total chlorine and the value free chlorine in the body of water but one does not determine a measured difference between the total chlorine and the free chlorine in the body of water as taught in the aforementioned "industry recommendations".

FIG. 1 shows that in the first step one determines if the value of the free chlorine (13), falls into any of three different ranges. In the first range (14) the free chlorine in the body of water is less than 0.5 ppm, in the second range (15) the free chlorine in the body of water is between 0.5 ppm to 1 ppm and in the third range (16) the free chlorine in the body of water is greater than 1 ppm. As used herein ppm refers to parts per million.

FIG. 1 shows that if the free chlorine is less than 0.5 ppm (14) one should proceed to follow industry recommendations on when to shock (17). Also if the free chlorine is greater than 1 ppm (16) one should also proceed to follow the industry recommendations on when to shock (17). As described herein industry recommendations on when to shock include recommendations from the following entities, which are based on the differences between the total chlorine and the free chlorine in the body of water and consist of the following "industry recommendations".

The American Chemistry Council recommendation, which advises owners the system should be shocked when the combined chlorine (CC) i.e. if (TC-FC) is greater than 0.2 ppm;

The National swimming Foundation CPO handbook that recommends to shock when the difference between the total available chlorine (TAC) and the free available chlorine (FAC) i.e. if (TC-FC) is greater that 0.3 ppm;

The Washington County MN fact sheet on "Proper Supper chlorination of pools" recommends the pool water should be shocked if the combined chlorine (CC) i.e. if (TC-FC) exceeds 1 ppm;

The Swim University publication that recommends one to keep the combined chloramines (CC) i.e. if (TC-FC) less than 0.2 ppm; and Bioguard, which sells a shock product, recommends that the "to prevent pool problems, shock at least once per week during periods of heavy use or when water temperatures are above 80° Fahrenheit and once every two weeks in resident pools receiving normal use".

Thus the above "industry recommendations", which are typical, rely on either the difference between the total chorine and the free chlorine or the use of the body of water as an indicator on when to shock the body of water. The method described herein does not.

In the next step (13) of the comparative method described herein one needs to make a comparison between the measured value of the total chlorine (TC) and the measured value of the free chlorine (FC). In this step one determines if the free chlorine (FC) is in a range of 0.5 ppm to 1 ppm (15), a range of less than 0.5 ppm (14), or a range greater than 1 ppm (16). FIG. 1 shows that if the free chlorine (FC) is in the range of less than 0.5 ppm (14) or the range of greater than 1 ppm (16) the "industry recommendations" on adding chlorine can be followed. However, if the free chlorine (FC) is in the range of 0.5 ppm to 1 ppm (15) additional steps need to be taken.

If the total chlorine (TC) is not 3 ppm greater than the free chlorine (FC) (18) the body of water does not contain a hydantoin (19). In that case one should follow the industry recommendation on when to shock the body of water (17).

However, if the total chlorine (TC) is 3 ppm greater than the free chlorine (FC) (20) it indicates that there is a hydantoin present (21) and that one should not follow industry recommendation on when to shock (22) but should proceed on adding chlorine based on the presence of a hydantoin in the body of water.

In the method described herein through measurements of the value of total chlorine in ppm in the body of water and value of free chlorine in ppm in the body or water and without relying on the differences between the total chlorine and the free chlorine one can determine when to add chlorine or shock a body of water with the recommendation taking into consideration that there may be a hydantoin within the body of water even though there has been no direct measurement or determination of the presence of a hydantoin in the body of water.

While the invention described herein is directed to maintaining a body of water for human immersion therein, such as a pool or hot tub, the invention may be also used for maintaining other bodies of water in a condition for human use without departing from the spirit and scope of the invention.

We claim:

1. A comparative method for maintaining a body of water for human immersion through addition of chlorine, where a sanitizing content of the body of water other than a presence of chlorine in the body of water is unknown comprising:
    measuring a free chlorine content in the body of water in ppm;
    measuring a total chlorine content in the body of water in ppm;
    determining if the free chlorine content body of water is within a range of 5 ppm to 1 ppm; and
    adding a batch of chlorine to the body of water based on an "industry recommendation" if the total chlorine content in the body of water is not 3 ppm greater than the free chlorine content in the body of water and the free chlorine content in the body of water is within the range of 5 ppm to 1 ppm.

2. The method of claim 1 wherein the "industry recommendation" is to shock the body of water if the total chlorine content in the body of water minus the free chlorine content in the body of water is not greater than 3 ppm.

3. The method of claim 1 including adding chlorine to the body of water based on the presence of a hydantoin in the body of water if the total chlorine content in the body of water is at least 3 ppm greater than the free chlorine in the body of water.

4. The method of claim 3 wherein a further batch of chlorine is added to the body of water where the further batch of chlorine is based on a hydantoin present in the body of water.

5. The method of claim 1 when the "industry recommendation" is based on a difference between the total chlorine content in the body of water in ppm and the free chlorine content in the body of water in ppm.

6. The method of claim 1 wherein the body of water for immersion is a hot tub body of water.

7. The method of claim 1 wherein the body of water for immersion is a swimming pool body of water.

8. A method of maintaining a safe level of chlorine in a body of water where the body of water is in a swimming pool and when a nonchlorine content of a sanitizer in the swimming pool is unknown comprising the steps of;
    testing the water in the swimming pool to determine a level of free available chlorine (FAC) in the water in the swimming pool in ppm;
    testing the water in the swimming pool to determine a level of total available chlorine (TAC) in the water in the swimming pool water in ppm;

determining if the free available chlorine (FAC) is within a range of 0.5 ppm to 1 ppm and the total available chlorine is at least 3 ppm greater than the free available chlorine; and adding chlorine to the swimming pool water based on the presence of a hydantoin in the body of water if the free available chlorine (FAC) is within the range of 0.5 ppm to 1 ppm and the total available chlorine is at least 3 ppm greater than the free available chlorine.

9. A method for maintaining a body of water for human immersion, where a hydantoin content of the body of water is unknown comprising:

measuring free chlorine content in the body of water;

measuring total chlorine content in the body of water;

determining if the free chlorine content body of water is within a range of 5 ppm to 1 ppm;

determining if the total chlorine content in the body of water is 3 ppm greater than the free chlorine content in the body of water and adding chlorine to the body of water based on the body of water containing a hydantoin;

adding chlorine to the body of water based on an industry recommendation if the free chlorine in the body of water is greater than 1 ppm.

10. The method of claim 9 for maintaining a body of water for human immersion, where a hydantoin content of the body of water is unknown comprising:

adding chlorine to the body of water based on an industry recommendation if the free chlorine content in the body of water is less than 0.5 ppm.

11. The method of claim 9 for maintaining a body of water for human immersion, where a hydantoin content of the body of water is unknown wherein adding chlorine to the body of water is sufficient to shock the body of water.

* * * * *